(12) United States Patent
Yamazoe (10) Patent No.: US 10,094,956 B2
(45) Date of Patent: Oct. 9, 2018

(54) OPTICAL FIELD ENHANCEMENT DEVICE AND MANUFACTURING METHOD OF THE SAME

(71) Applicant: FUJIFILM Corporation, Tokyo (JP)

(72) Inventor: Shogo Yamazoe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 349 days.

(21) Appl. No.: 14/849,932

(22) Filed: Sep. 10, 2015

(65) Prior Publication Data

US 2016/0003988 A1 Jan. 7, 2016

Related U.S. Application Data

(63) Continuation of application No. PCT/JP2014/001617, filed on Mar. 20, 2014.

(30) Foreign Application Priority Data

Mar. 27, 2013 (JP) .................. 2013-066604

(51) Int. Cl.
*G02F 1/03* (2006.01)
*G02B 26/00* (2006.01)
(Continued)

(52) U.S. Cl.
CPC ............. *G02B 5/008* (2013.01); *B82Y 20/00* (2013.01); *G01N 21/554* (2013.01); *B82Y 30/00* (2013.01); *B82Y 40/00* (2013.01)

(58) Field of Classification Search
CPC ......... B82Y 25/00; B82Y 20/00; B82Y 30/00; G02B 5/23; G02F 1/133615; G02F 1/31;
(Continued)

(56) References Cited

U.S. PATENT DOCUMENTS

2003/0231304 A1 12/2003 Chan et al.
2004/0161369 A1 8/2004 Chan et al.
(Continued)

FOREIGN PATENT DOCUMENTS

EP 1 857 810 A1 11/2007
JP 2005-172569 A 6/2005
(Continued)

OTHER PUBLICATIONS

Japanese Office Action and English translation thereof, dated Sep. 20, 2016, for Japanese Application No. 2013-066604.
(Continued)

*Primary Examiner* — Dawayne A Pinkney
(74) *Attorney, Agent, or Firm* — Birch, Stewart, Kolasch & Birch, LLP (57) ABSTRACT

In an optical field enhancement device in which localized plasmon is induced on a surface through illumination of excitation light and intensity of signal light emitted, by the illumination, from a sample placed on the surface is enhanced, forming sharp-edged petal-like fine uneven structures disposed at random on a substrate, and forming plate-like metal fine structures on tip portions of the sharp-edged petal-like fine uneven structures by depositing a metal from an oblique direction with respect to a direction perpendicular to a plane of the substrate on which the sharp-edged petal-like fine uneven structures are formed.

12 Claims, 8 Drawing Sheets (51) Int. Cl.
  *B05D 5/00* (2006.01)
  *B32B 9/00* (2006.01)
  *G02B 5/00* (2006.01)
  *B82Y 20/00* (2011.01)
  *G01N 21/552* (2014.01)
  *B82Y 30/00* (2011.01)
  *B82Y 40/00* (2011.01)

(58) Field of Classification Search
  CPC ........... G02F 1/0102; G03H 3/00; G11B 7/24; G11B 5/7021; G09F 3/00; B60R 1/088; H04N 9/3137; H04N 13/0497; C23C 24/04; H05K 3/381; H01J 29/14; H01J 29/89; C04B 28/14; C04B 41/009; G01S 7/5206; G03B 21/00; C09D 5/185
  USPC ....... 359/241, 244, 267, 318, 277, 240, 237, 359/242; 427/7, 256, 127, 201, 444; 428/703, 689, 704, 843; 348/902, 832, 348/163; 353/29, 84; 349/62; 367/8; 430/270.11; 345/6, 32
  See application file for complete search history.

(56) References Cited

U.S. PATENT DOCUMENTS

| | | |
|---|---|---|
| 2005/0105085 A1 | 5/2005 | Naya |
| 2009/0279084 A1 | 11/2009 | Suzuki et al. |
| 2011/0166045 A1 | 7/2011 | Dhawan et al. |
| 2013/0027698 A1 | 1/2013 | Li et al. |
| 2013/0182343 A1 | 7/2013 | Naya et al. |
| 2014/0016127 A1 | 1/2014 | Yamazoe et al. |
| 2014/0034235 A1 | 2/2014 | Yamazoe et al. |

FOREIGN PATENT DOCUMENTS

| | | |
|---|---|---|
| JP | 2006-514286 A | 4/2006 |
| JP | 2006-145230 A | 6/2006 |
| JP | 2007-501391 A | 1/2007 |
| JP | 2008-232806 A | 10/2008 |
| JP | 4347801 B2 | 10/2009 |
| JP | 2010-230352 A | 10/2010 |
| JP | 2011-077868 A | 4/2011 |
| JP | 4783907 B2 | 9/2011 |
| JP | 2012-063293 A | 3/2012 |
| JP | 2012-211839 A | 11/2012 |
| WO | WO 2005/017570 A2 | 2/2005 |
| WO | WO 2011/133144 A1 | 10/2011 |
| WO | WO 2012/015443 A1 | 2/2012 |
| WO | WO 2012/024006 A2 | 2/2012 |
| WO | WO 2012/127841 A1 | 9/2012 |

OTHER PUBLICATIONS

Japanese Office Action dated Mar. 1, 2016 in corresponding JP Application No. 2013-066604 with an English Translation.
Ghadarghadr et al., "Plasmonic array nanoantennas on layered substrates: modeling and radition characteristics", Optics Express, vol. 17, No. 21, pp. 18556-18570, Oct. 12, 2009.
International Search Report issued in PCT/JP2014/001617 dated Jun. 24, 2014.
Written Opinion of the International Searching Authority issued in PCT/JP2014/001617 dated Jun. 24, 2014.

80° DEPOSITION

FIG.7

0° DEPOSITION

OPTICAL FIELD ENHANCEMENT DEVICE AND MANUFACTURING METHOD OF THE SAME

CROSS-REFERENCE TO RELATED APPLICATIONS

This application is a Continuation of PCT International Application. No. PCT/JP2014/001617 filed on Mar. 20, 2014, which claims priority under 35 U.S.C. § 119 (a) to Japanese Patent Application No. 2013-066604 filed on Mar. 27, 2013. Each of the above application(s) is hereby expressly incorporated by reference, in its entirety, into the present application.

BACKGROUND

The present invention relates to an optical field enhancement device with a fine metal structure capable of inducing localized plasmon and a manufacturing method of the same.

Field enhancement devices, such as sensor devices, Raman spectroscopy devices, and the like, that utilize a field enhancement effect of a localized plasmon resonance phenomenon on a surface of a metal are known. The Raman spectroscopy is a method of obtaining a Raman scattered light spectrum (Raman spectrum) by separating scattered light obtained by illuminating single wavelength light onto a substance, and it is used for identifying a substance or the like.

Raman spectroscopy includes a method that utilizes an optical field enhanced by localized plasmon resonance, called surface enhanced Raman scattering (SERS), to enhance weak Raman scattered light (refer to S. Ghadarghadr et al., "Plasmonic array nanoantennas on layered substrates: modeling and radiation characteristics", OPTICS EXPRESS, Vol. 17, No. 21, pp. 18556-18570, 2009). This makes use of the principle that when light is illuminated onto a metal body, in particular, onto a metal body having a nano-order uneven pattern on a surface with a substance being in contact with the surface, optical field enhancement occurs due to localized plasmon resonance and the intensity of Raman scattered light of the sample in contact with the surface of the metal body is enhanced. The surface enhanced Raman spectroscopy may be performed using a substrate having an uneven metal structure on a surface as a carrier (substrate) for carrying a subject.

As for substrates having metal fine uneven structures on a surface, a substrate manufactured by forming an uneven pattern on a surface of a Si substrate and forming a metal film on the surface of the uneven pattern is mainly used (refer to PCT Japanese Publication No. 2006-514286, Japanese Patent No. 4347801, and Japanese Unexamined Patent Publication No. 2006-145230).

Further, a substrate manufactured by anodizing a surface of an Al substrate to turn a portion into a metal oxide ($Al_2O_3$) layer and filling a metal in a plurality of fine pores spontaneously formed in the metal oxide layer during the anodizing process and opens at the surface of the metal oxide layer is also proposed (refer to Japanese Unexamined Patent Publication No. 2005-172569).

SUMMARY

But, manufacture of fine uneven structures using photolithography and etching, as described in PCT Japanese Publication No. 2006-514286, Japanese Patent No. 4347801, and Japanese Unexamined Patent Publication No. 2006-145230, or manufacture of metal uneven structures using anodization, as described in Japanese Unexamined Patent Publication No. 2005-172569, is considered that the substrate cost per unit area is increased because such methods of manufacturing fine uneven structures or metal uneven structures are complicated and difficult to obtain substrates having large areas.

In the meantime, in Japanese Patent No. 4783907, an optical field enhancement substrate is manufactured by depositing a transparent substance from an oblique direction with respect to a substrate to form a fine uneven structure having anisotropy and further depositing a precious metal thereon from an oblique direction. This method involves only a manufacturing process of deposition, but it cannot be said to be a simple manufacturing method because the deposition needs to be performed by changing the deposition direction several times. In addition, since the fine uneven structure has anisotropy, so does the fine structure of precious metal, whereby the plasmon resonance wavelength differs depending on the polarization direction of the excitation light and the Raman scattered light intensity depends largely on the polarization direction. Therefore, when using the substrate, it is necessary to adjust the polarization of the excitation light, which is a factor of signal intensity variation in quantitative measurement.

In Japanese Unexamined Patent Publication No. 2011-077868 and Japanese Unexamined Patent Publication No. 2012-063293, a fine uneven structure of a metal is formed by forming an aluminum film on a substrate, then boiling the substrate in deionized water to form a sharp-edged petal-like fine uneven structure called boehmite on the substrate, and depositing gold on the boehmite. This metal fine uneven structure has optical isotropy and obtains Raman scattered light of substantially the same intensity for the excitation light of any polarization.

Figure 12:
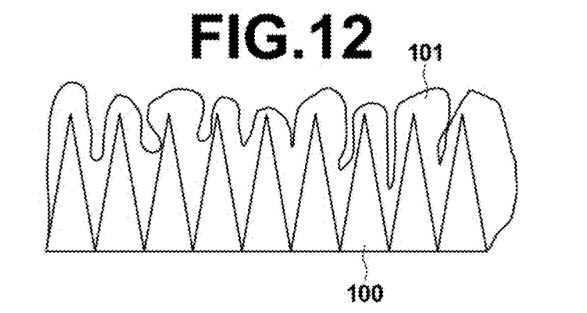
FIG. 12 is a schematic cross-sectional view of a substrate in which gold is deposited on boehmite fine uneven structures from a direction perpendicular to the structures.

But, as shown in FIG. 12, because the gold is deposited from a direction perpendicular to the substrate, gold 101 is filled in concave portions of boehmite fine uneven structures 100. If the gold is filled in the concave portions in this way, the Raman light coming out to the substrate side is reduced by being absorbed or scattered by the gold in the concave portions when SERS measurement is performed from the substrate side. Further, they are not fine structures of isolated masses of the gold on the convex portions but rather each mass contacts with each other to form almost a single thin film. If that is the case, localization of the plasmon decreases, leading to reduced enhancement.

Further, in PCT Japanese Publication No. 2007-501391, Japanese Unexamined Patent Publication No. 2008-232806, and Japanese Unexamined Patent Publication No. 2010-230352, an optical field enhancement substrate is manufactured by performing deposition from an oblique direction, as in Japanese Patent No. 4347801. But they do not disclose a method for giving optical isotropy to fine uneven structures. In view of the circumstances described above, it is an object of the present invention to provide a high sensitivity optical field enhancement device with suppressed optical anisotropic orientation and a manufacturing method of the same.

An optical field enhancement device of the present invention is a device in which localized plasmon is induced on a surface through illumination of excitation light and intensity of signal light emitted, by the illumination, from a sample placed on the surface is enhanced, the device including sharp-edged petal-like fine uneven structures disposed at random on a substrate and plate-like metal fine structures formed on tip portions of the sharp-edged petal-like fine uneven structures.

In the optical field enhancement device described above, the plate-like metal fine structures may have a ratio of average length to average thickness greater than or equal to two.

Further, the sharp-edged petal-like fine uneven structures may be formed of a hydrate of a metal.

Still further, aluminum or titanium may be used as the metal described above.

Further, the sharp-edged petal-like fine uneven structures may be formed of a hydrate of a metal oxide.

Still further, an aluminum oxide, a titanium oxide, or a magnesium oxide may be used as the metal oxide.

Further, the plate-like metal fine structures may be formed of gold, silver, copper, platinum, or aluminum.

Still further, a metal film formed of chromium, titanium, nickel, iron, silver, aluminum, germanium, or a metal suboxide may be provided between the sharp-edged petal-like fine uneven structures and the plate-like metal fine structures.

A manufacturing method of an optical field enhancement device of the present invention is a manufacturing method of an optical field enhancement device in which localized plasmon is induced on a surface through illumination of excitation light and intensity of signal light emitted, by the illumination, from a sample placed on the surface is enhanced, the method including the steps of forming sharp-edged petal-like fine uneven structures disposed at random on a substrate, and forming plate-like metal fine structures on tip portions of the sharp-edged petal-like fine uneven structures by depositing a metal from an oblique direction with respect to a direction perpendicular to a plane of the substrate on which the sharp-edged petal-like fine uneven structures are formed.

In the manufacturing method of an optical field enhancement device described above, the metal may be deposited from a direction tilted greater than or equal to 65° with respect to the direction perpendicular to the plane of the substrate.

Further, in the manufacturing method of an optical field enhancement device described above, the metal may be deposited with a deposited film thickness of 10 nm to less than 60 nm.

Still further, before depositing the metal, chromium, titanium, nickel, iron, silver, aluminum, germanium, or a metal suboxide may be deposited on the sharp-edged petal-like fine uneven structures.

According to the optical field enhancement device and the manufacturing method of the same, in an optical field enhancement device in which localized plasmon is induced on a surface through illumination of excitation light and intensity of signal light emitted, by the illumination, from a sample placed on the surface is enhanced, sharp-edged petal-like fine uneven structures disposed at random on a substrate are formed, and plate-like metal fine structures are formed on tip portions of the sharp-edged petal-like fine uneven structures by depositing a metal from an oblique direction with respect to a direction perpendicular to the plane of the substrate on which the sharp-edged petal-like fine uneven structures are formed. This allows the optical field enhancement device to have high sensitivity with suppressed optical anisotropy.

Further the deposition of a metal from an oblique direction allows isolated plate-like metal fine structures to be formed on the sharp-edged petal-like fine uneven structures. This may increase the field enhancement and light may be detected from the substrate side with high sensitivity.

Forming plate-like metal fine structures on the sharp-edged petal-like fine uneven structures may increase the Q-value of plasmon in comparison with spherical structures and is preferable for field enhancement.

Further, forming the plate-like metal fine structures on tip portions of the sharp-edged petal-like fine uneven structures reduces contact areas with the metal structures more than the case in which the plate-like metal fine structures are formed on columnar structures or spherical structures, whereby plasmon energy loss from the contact areas may be reduced.

DETAILED DESCRIPTION OF THE PREFERRED EMBODIMENTS

Hereinafter, an embodiment of the optical field enhancement device and the manufacturing method of the same of the present invention will be described with reference to the accompanying drawings. Note that each component in the drawings is not necessarily drawn to scale for ease of visual recognition.

Figure 1A:
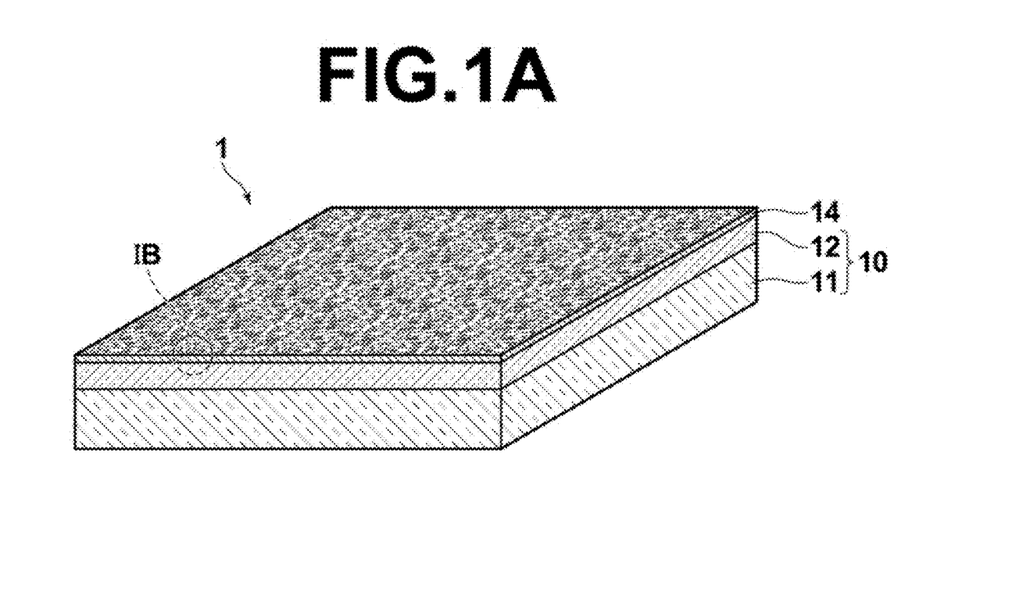
FIG. 1A is a perspective view of an optical field enhancement substrate, which is an embodiment of the optical field enhancement device of the present invention.
Figure 1B:
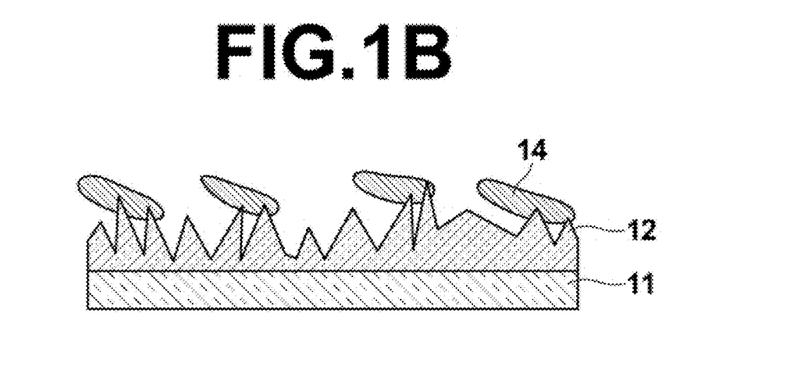
FIG. 1B is an enlarged view of a portion IB of a side surface of the optical field enhancement substrate shown in FIG. 1A.

FIG. 1A is a perspective view of an optical field enhancement substrate 1, which is an embodiment of the optical field enhancement device of the present invention. FIG. 1B is an enlarged view of a portion IB of a side surface of the optical field enhancement substrate 1 shown in FIG. 1A. The optical field enhancement substrate 1 of the present embodiment is a substrate in which localized plasmon is induced on a surface through illumination of excitation light and intensity of signal light emitted, by the illumination, from a sample placed on the surface is enhanced.

More specifically, the optical field enhancement substrate 1 includes a sharp-edged petal-like fine uneven structure layer 12 having sharp-edged petal-like fine uneven structures formed on a surface of a transparent substrate 10, and a metal fine structure layer 14 having plate-like metal fine structures formed on tip portions of the sharp-edged petal-like fine uneven structure layer 12, as illustrated in FIGS. 1A and 1B.

The substrate 10 includes a substrate body 11 made of glass or resin, and the sharp-edged petal-like fine uneven structure layer 12 is formed on the substrate body 11.

The sharp-edged petal-like fine uneven structure layer 12 is made of a metal oxide hydrate or a metal hydrate. More specifically, for example, alumina hydrates may be used and more particularly, an alumina monohydrate called boehmite (expressed as $Al_2O_3 \cdot H_2O$ or $AlOOH$) and an alumina trihydrate (aluminum hydrate) called bayerite (expressed as $Al_2O_3 \cdot 3H_2O$ or $Al(OH)_3$) may be used. In addition, the layer may also be formed of hydrates of titanium, titanium oxide, and magnesium oxide ($Ti \cdot H_2O$, $TiO_2 \cdot H_2O$, $MgO \cdot H_2O$).

The sharp-edged petal-like fine uneven structure layer 12 is transparent and includes sharp-edged petal-like structures having different sizes (apex angles) and different orientations disposed at random, as illustrated in FIG. 1B.

Figure 2:
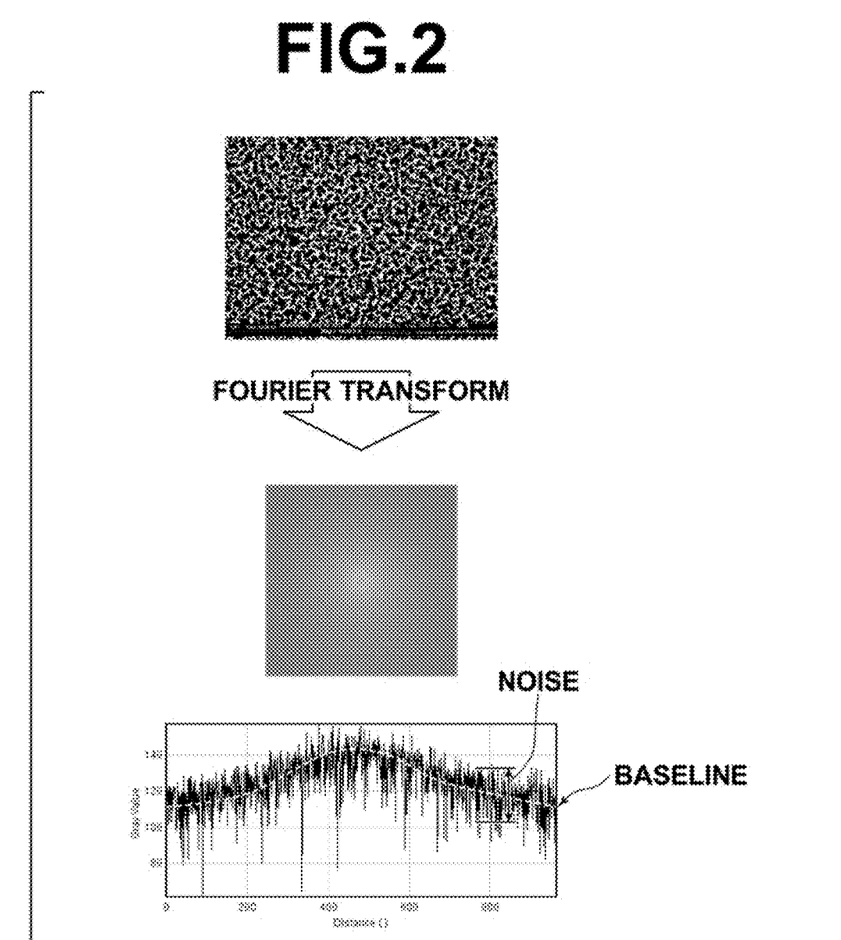
FIG. 2 shows an example of a Fourier transform result of a SEM image of a sharp-edged petal-like fine uneven structure layer.

The term "sharp-edged petal-like structure" as used herein is a structure whose fine structure cross-sectional area of a plane parallel to the substrate surface decreases as the distance from the substrate surface increases. The randomness of the sharp-edged petal-like structure is preferably as follows. That is, when an image obtained by binarizing a SEM image of the sharp-edged petal-like fine uneven structure layer 12 captured by imaging from the upper surface is Fourier transformed, the structure preferably does not have an intensity peak greater than or equal to twice the standard deviation value of the baseline intensity taken as noise value in the Fourier transformed intensity distribution. FIG. 2 shows an example of a Fourier transform result of an image obtained by binarizing a SEM image.

The sharp-edged petal-like fine uneven structure of the sharp-edged petal-like fine uneven structure layer 12 may be any structures whose average period (average pitch) and average depth are smaller than the wavelength of the excitation light and allow a metal fine structure layer 14, to be described later, to be formed thereon. As the excitation light, ordinary visible light is used. Here, in the sharp-edged petal-like fine uneven structure layer 12, the average period refers to an average value of distances between the most adjacent tips of the sharp-edged petal-like structures, and the average depth refers to an average value of distances from tip portions to adjacent bottom portions of the sharp-edged petal-like structures.

More specifically, the average period and the average depth of the sharp-edged petal-like fine structures are in the order of several tens of nanometers to several hundreds of nanometers, and both the average period and the average depth are preferably less than or equal to 200 nm. Further, both the average period and the average depth are preferably 10 to 150 nm to efficiently generate an enhanced optical field.

As illustrated in FIG. 1B, the metal fine structure layer 14 includes many plate-like metal fine structures formed on tip portions of the sharp-edged petal-like fine uneven structure layer 12. The plate-like metal fine structures are formed by depositing a metal from an oblique direction with respect to a direction perpendicular to a plane of the substrate on which the sharp-edged petal-like fine uneven structure layer 12 is formed. The plate-like metal fine structures have various shapes, but the aspect ratio of average length to average thickness of the plate-like metal fine structures (average length/average thickness) is preferably greater than or equal to two. The calculation method of the average thickness and the average length will be described later in detail.

Each of the plate-like metal fine structures is formed in isolation and a gap is provided between plate-like metal fine structures. Therefore, the metal fine structure layer 14 as a whole is in an insulated state without having conductivity.

The plate-like metal fine structure may be made of any material as long as it can generate localized plasmon by receiving excitation light, and gold (Au), silver (Ag), copper (Cu), aluminum (Al), platinum (Pt), or an alloy consisting primary of these is preferably used. In particular, Au or Ag is more preferable.

Figure 3:
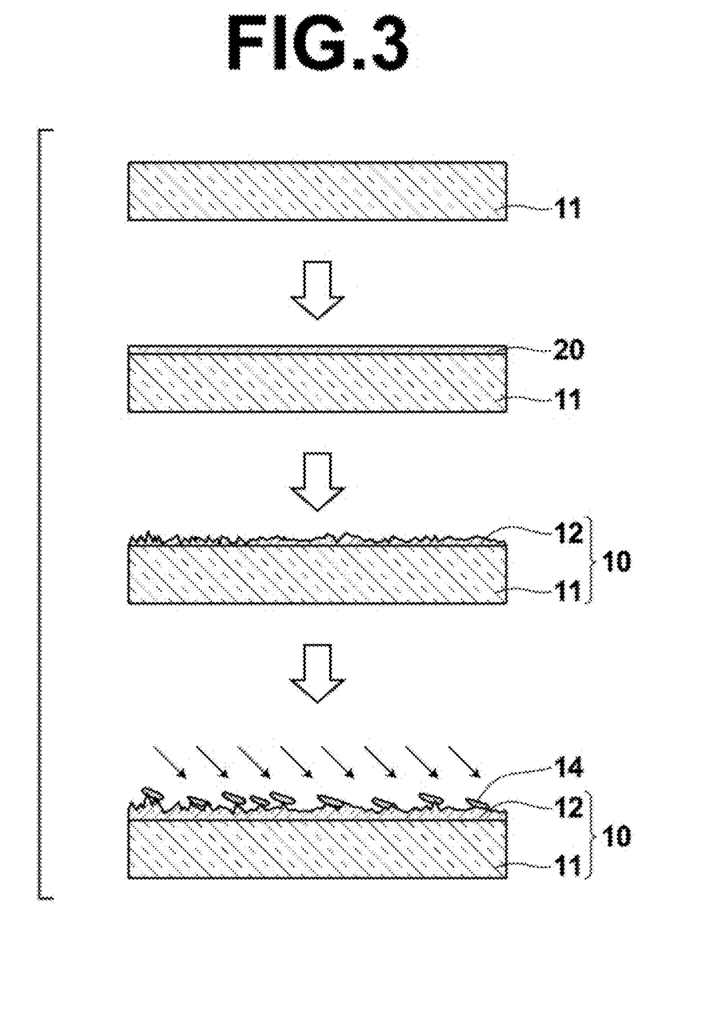
FIG. 3 is a drawing for explaining a manufacturing process of the optical field enhancement substrate of the present embodiment.

Next, a manufacturing method of the optical field enhancement substrate 1 of the present embodiment will be described. FIG. 3 shows a manufacturing process of the optical field enhancement substrate 1 of the present embodiment, illustrating a cross-sectional view of the substrate in each process step.

As the substrate body 11, a glass substrate (BK-7: manufactured by Corning, Eagle 2000) was used.

The substrate body 11 was subjected to ultrasonic cleaning (45 kHz) using an alkaline cleaning solution (semi-coclean) and an aluminum layer 20 is formed on the substrate body 11 with a thickness of 50 nm using a spattering system (manufactured by Canon ANELVA Corporation). The thickness of the aluminum was measured using a surface shape measuring instrument (manufactured by TENCOR Inc.) and confirmed that the thickness was 50 nm (±10%).

Figure 4:
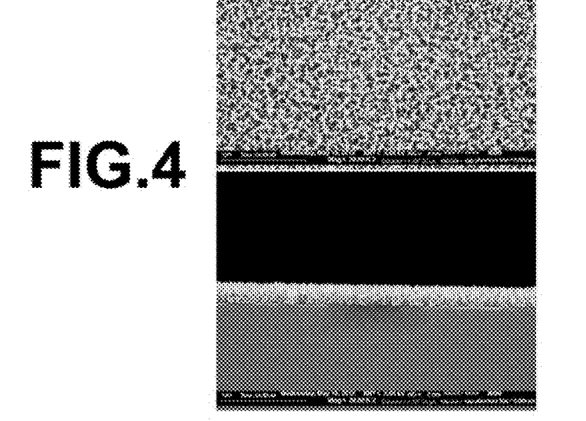
FIG. 4 shows a SEM observation result of a surface of the sharp-edged petal-like fine uneven structure layer.

Thereafter, deionized water was prepared in a water bath (Nishi Seiki K. K.) and boiled, then the substrate body 11 with the aluminum layer 20 formed thereon was immersed in the boiling water, and taken out after ten minutes. At this time, it was confirmed that the aluminum turned to transparent about three to four minutes after the substrate body 11 with the aluminum layer 20 formed thereon was immersed in the boiling water. The reason for this is that the aluminum turned to sharp-edged petal-like fine uneven structures of bayerite or boehmite by the boiling process (boehmite treatment). FIG. 4 shows an observation result of the surface of the sharp-edged petal-like fine uneven structure layer 12 by a SEM (S4100, manufactured by Hitachi, Ltd.). FIG. 4 shows a top view on the upper side and a cross-sectional view on the lower side.

According to the cross-sectional view on the lower side of FIG. 4, it has petal structures of boehmite like flower petals. Further, the observation from above shows that the petal structures are joined, forming sharp-edged petal-like structures with the joined portions being the apexes.

Since the boehmite has such sharp-edged petal-like structures, and the cross-sectional area of the boehmite decreases as the distance from the substrate body 11 increases and the effective refractive index decreases continuously, the boehmite layer also functions as an antireflection film.

Here, aluminum is used as the metal subjected to the hydrothermal reaction, but other metals described above may also be used. Further, it is also possible to form sharp-edged petal-like fine uneven structures using a metal oxide, such as alumina ($Al_2O_3$), in the same way. Although, the present embodiment uses sputtering as the method of layering these metals on the substrate body 11, heating evaporation method or sol-gel method may also be used.

Further, as the hydrothermal reaction, the substrate body 11 with the aluminum layer 20 formed thereon is boiled, but the substrate body 11 with the aluminum layer 20 formed thereon may be subjected to a process in which it is reacted with high temperature vapor. As the method of manufacturing sharp-edged petal-like fine uneven structures, the method of producing boehmite that can be achieved by subjecting a metal or a metal oxide to hydrothermal reaction is more preferable, since it allows easy manufacture of device having a large area.

Lastly, a metal fine structure layer 14 having plate-like metal fine structures was formed on the sharp-edged petal-like fine uneven structure layer 12 by depositing gold (Au) from a direction tilted by 80° with respect to a direction perpendicular to a plane of the substrate on which the sharp-edged petal-like fine uneven structure layer 12 is formed with a thickness of 25 nm by electric beam (EB) deposition.

Figure 5:
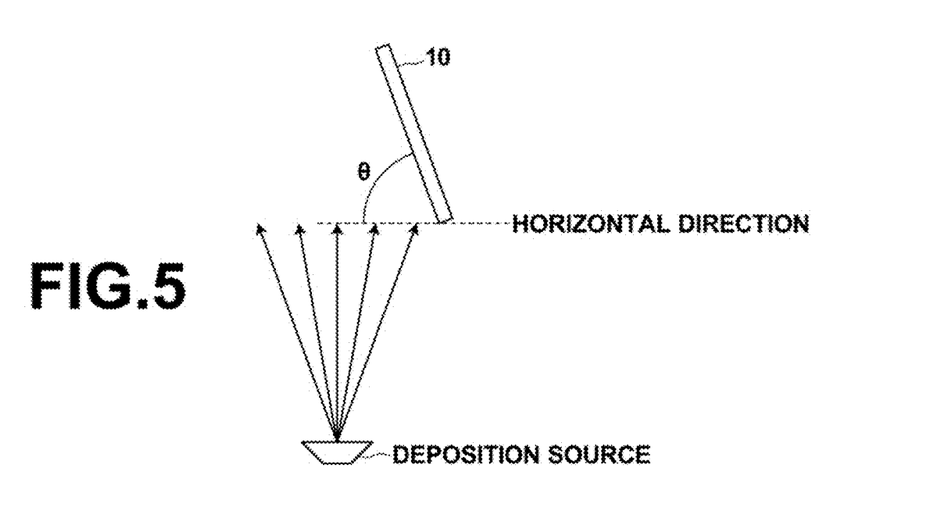
FIG. 5 is a drawing for explaining oblique deposition.

The oblique deposition from the 80° direction described above is performed, more specifically, by tilting the substrate 10 with respect to the deposition source placed horizontally, as illustrated in FIGS. 5, and θ may be set to 80° in this case. Hereinafter, θ is referred to as the deposition angle.

Here, the deposited film thickness is measured in the following manner. That is, another glass substrate washed in the same manner as the substrate body 11 described above was masked with a tape, then the masked glass substrate was placed in the deposition system simultaneously with the substrate 10 with the sharp-edged petal-like fine uneven structure layer 12 formed thereon to deposit the metal on the glass substrate, and the tape was peeled off to measure the step of the deposited metal film as the thickness.

Figure 6:
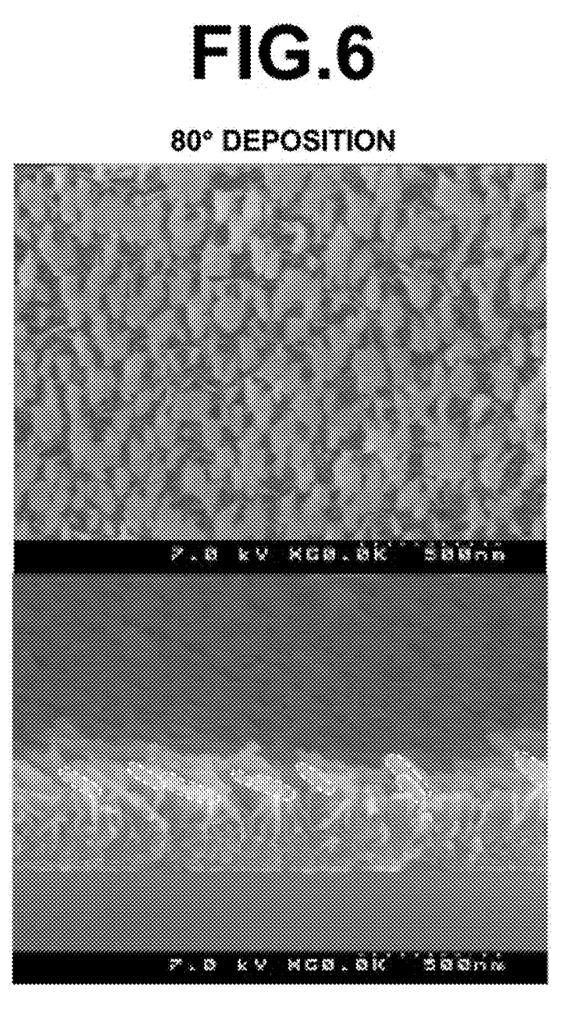
FIG. 6 shows a SEM observation result of an optical field enhancement substrate with plate-like metal fine structures formed thereon.

FIG. 6 shows an observation result of the optical field enhancement substrate 1 with the metal fine structure layer 14 formed thereon by a SEM (S 4100, manufactured by Hitachi Ltd.). FIG. 6 shows a top view on the upper side and a cross-sectional view on the lower side. In the top view, pale gray portions are plate-like metal fine structures and dark gray portions are surfaces of the sharp-edged petal-like fine uneven structure layer 12, serving as the under layer of the metal fine structure layer 14.

In the case where the metal fine structure layer 14 is formed by the oblique deposition with a deposition angle of 80°, a gap is formed between plate-like metal fine structures and surfaces of the under layer, sharp-edged petal-like fine uneven structure layer 12 can be seen, as shown in FIG. 6. In addition, the SEM image in the cross-sectional view shows that plate-like metal fine structures (indicated by dotted lines) are formed on tip portions of the sharp-edged petal-like fine uneven structures by the oblique deposition with the deposition angle of 80°.

Measurement of electrical resistance of the optical field enhancement substrate 1 with plate-like metal fine structures formed thereon by the oblique deposition with the deposition angle of 80° showed that the substrate 1 was in an insulated state, because the plate-like metal fine structures of gold form isolated masses.

Figure 7:
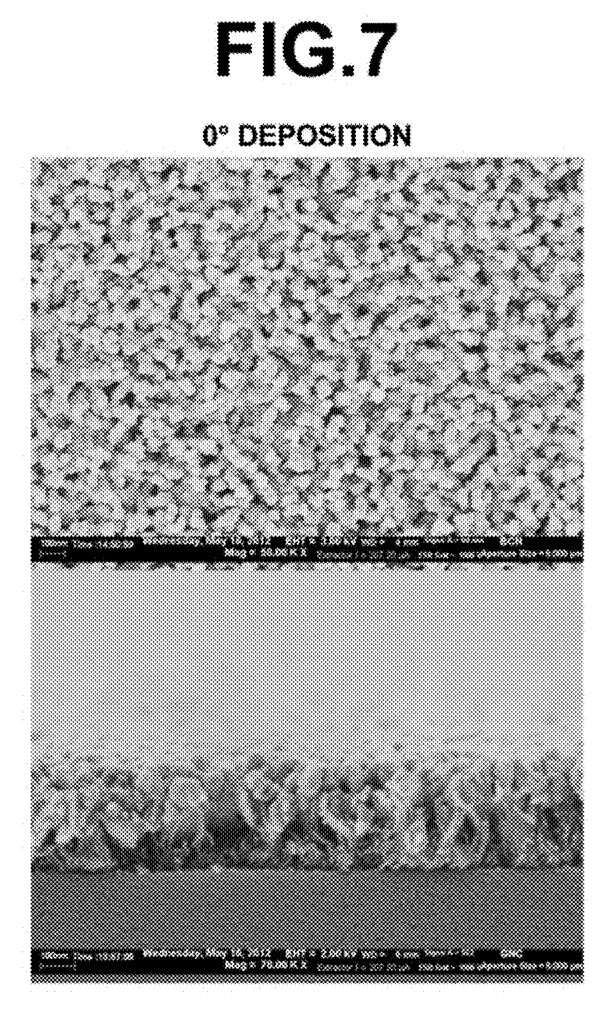
FIG. 7 shows a SEM observation result of an optical field enhancement substrate on which metal fine uneven structures are formed by performing deposition from a direction perpendicular to the substrate.

In the meantime, another optical field enhancement substrate with a metal fine uneven structure formed thereon was obtained for comparison by depositing gold (Au) on the surface of a sharp-edged petal-like fine uneven structure layer identical to the present embodiment from a direction perpendicular to a plane of the substrate (deposition angle of 0°) with a thickness of 32 nm by electric beam (EB) deposition. FIG. 7 shows an observation result of the optical field enhancement substrate with the metal fine uneven structure formed thereon by a SEM (S4100, manufactured by Hitachi, Ltd.). FIG. 7 shows a top view on the upper side and a cross-sectional view on the lower side.

In the case where a metal fine uneven structure is formed by the deposition with the deposition angle of 0°, it is known that gold is deposited over the entire sharp-edged petal-like fine uneven structure layer without any gap, as shown in FIG. 7.

Measurement of electrical resistance of the optical field enhancement substrate with the metal fine uneven structure formed thereon showed that the substrate was in a conduction state with an electrical resistance of 23Ω.

The plate-like metal fine structures are likely to be peeled off from the sharp-edged petal-like fine uneven structures, since the metal of the plate-like metal fine structures is agglomerated only on tip portions of the sharp-edged petal-like fine uneven structures, as shown in FIG. 6. Therefore, after forming the sharp-edged petal-like fine uneven structures and before forming the plate-like metal fine structures, chromium, titanium, nickel, iron, silver, aluminum, germanium, or a metal suboxide, such as a cuprous oxide ($Cu_2O$), is preferably deposited on the sharp-edged petal-like fine uneven structures to form a film of such metal. This may improve the adhesiveness between the sharp-edged petal-like fine uneven structures and plate-like metal fine structures, whereby the durability of the structures may be improved.

Next, measurement results of Raman scattered light using the optical field enhancement substrate 1 produced in the foregoing manner will be described.

Using a measurement sample prepared by dropping and drying a solution of Rhodamine 6G in ethanol ($100 \times 10^{-6}$ mol/L) on the optical field enhancement substrate 1 as the subject, Raman scattered light was measured.

Raman scattered light was detected using a microscopic laser Raman spectrometer (HR800, manufactured by HIROBA Co., Ltd.). Laser light having a peak wave length of 785 nm was used as the excitation light and observation was performed with a 60× objective lens. The laser power immediately after the objective lens was 0.5 mW. The illumination time was three seconds.

Figure 8:
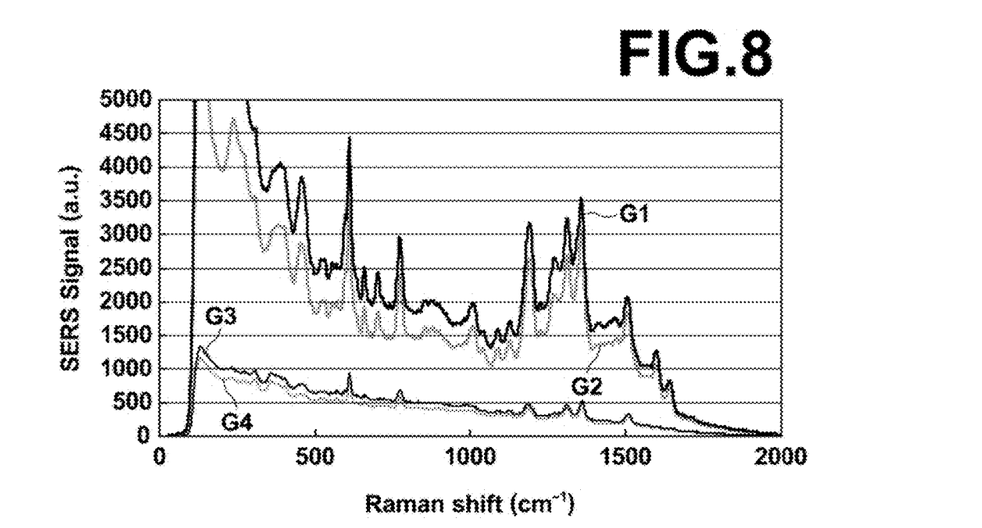
FIG. 8 is a graph showing Raman shift spectral distributions of optical field enhancement substrates manufactured at deposition angles of 80° and 0° respectively.
Figure 9:
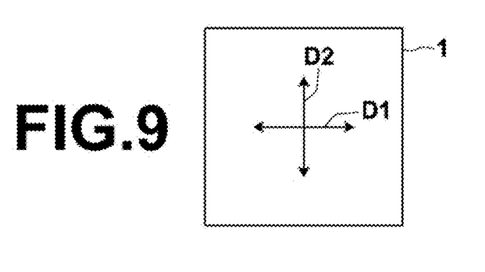
FIG. 9 is a drawing for explaining polarization of excitation light when detecting the Raman shift spectral distributions.

FIG. 8 is a graph showing Raman shift spectral distributions detected by the microscopic laser Raman spectrometer. Here, Raman shift spectral distributions were detected in two cases, one of which was when the excitation light was polarized parallel D1 to the deposition tilt direction and the other of which is when the excitation light was polarized perpendicular D2 to the deposition tilt direction, as illustrated in FIG. 9. The graph G1 in FIG. 8 shows a Raman spectral distribution when the deposition angle is 80° and the polarization direction of the excitation light is parallel D1, while the graph G2 shows a Raman spectral distribution when the deposition angle is 80° and the polarization direction of the excitation light is perpendicular D2. The graph G3 in FIG. 8 shows a Raman spectral distribution when the deposition angle is 0° and the polarization direction of the excitation light is parallel D1, while the graph G4 shows a Raman spectral distribution when the deposition angle is 0° and the polarization direction of the excitation light is perpendicular D2.

The graphs G1 to G4 of FIG. 8 show that the use of oblique deposition allows the Raman intensity to be enhanced by nine times. Further, it is also known that the plate-like metal fine structures have optical isotropy, as they are formed in random shapes, and this may suppress the polarization dependent variation in the spectral intensity to 30% or less. More specifically, for example, the peak intensity at 1360 cm$^{-1}$ after removal of background noise is 2955 in the graph G1 while 2193 in the graph G2, indicating that the reduction is suppressed to about 25%.

Figure 10:
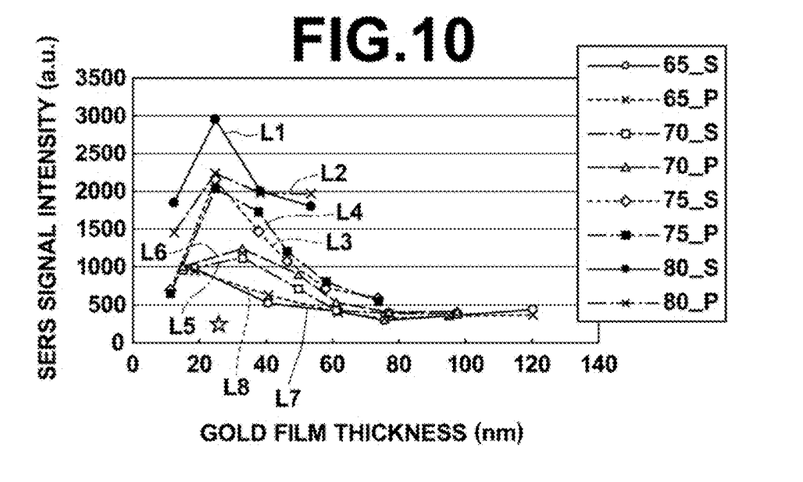
FIG. 10 shows Raman spectral measurement results of optical field enhancement substrates manufactured by changing the deposited film thickness and deposition angle when forming plate-like metal fine structures.

Next, Raman spectroscopic measurement results using optical field enhancement substrates produced by changing the deposited film thickness and deposition angle when forming plate-like metal fine structures will be described. Optical field enhancement substrates were produced in the same manner as the optical field enhancement substrate 1 described above on the following deposition angle and film thickness conditions and Raman measurements were performed, the results of which are shown in FIG. 10. The vertical axis in FIG. 10 represents the peak intensity of the obtained spectra at 1360 cm$^{-1}$ after removal of background noise.

The graph L1 shows a case where the deposition angle is 80°, deposited film thicknesses are 12 nm, 24 nm, 38 nm, and 54 nm, and polarization of the excitation light is parallel D1, while the graph L2 shows a case where the deposition angle is 80°, deposited film thicknesses are 12 nm, 24 nm, 38 nm, and 54 nm, and polarization of the excitation light is perpendicular D2.

The graph L3 shows a case where the deposition angle is 75°, deposited film thicknesses are 10 nm, 24 nm, 37 nm, 46 nm, 58 nm, and 74 nm, and polarization of the excitation light is parallel D1, while the graph L4 shows a case where the deposition angle is 75°, deposited film thicknesses are 10 nm, 24 nm, 37 nm, 46 nm, 58 nm, and 74 nm, and polarization of the excitation light is perpendicular D2.

The graph L5 shows a case where the deposition angle is 70°, deposited film thicknesses are 15 nm, 33 nm, 49 nm, 61 nm, 77 nm, and 97 nm, and polarization of the excitation light is parallel D1, while the graph L6 shows a case where the deposition angle is 70°, deposited film thicknesses are 15 nm, 33 nm, 49 nm, 61 nm, 77 nm, and 97 nm, and polarization of the excitation light is perpendicular D2.

The graph L7 shows a case where the deposition angle is 65°, deposited film thicknesses are 18 nm, 40 nm, 61 nm, 75 nm, 95 nm, and 120 nm, and polarization of the excitation light is parallel D1, while the graph L8 shows a case where the deposition angle is 65°, deposited film thicknesses are 18 nm, 40 nm, 61 nm, 75 nm, 95 nm, and 120 nm, and polarization of the excitation light is perpendicular D2.

FIG. 10 also shows a peak intensity when the deposition angle is 0° by a star mark. As FIG. 10 shows, the deposited film thickness may be set to from 10 nm to less than 60 nm and the deposition angle may be set to 65° or greater to obtain a signal intensity which is two or more times the peak intensity when the deposition angle is 0°. Note that, at that time, the interval between the tips of the sharp-edged petal-like fine uneven structure was 100 nm in average and the average thickness was 150 nm.

Figure 11:
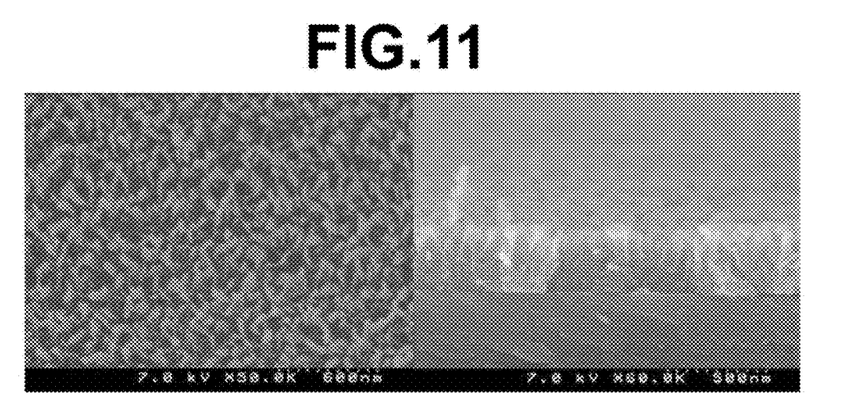
FIG. 11 shows an SEM image of an optical field enhancement substrate manufactured with a deposited film thickness of 10 nm and a deposition angle of 75°.

The reason for the decrease in signal intensity in the case where the deposited film thickness is thin may be considered that the aspect ratio of the average length to the average thickness (average length/average thickness) of plate-like metal fine structures formed on the sharp-edged petal-like fine uneven structures is small. FIG. 11 shows a SEM image of the optical field enhancement substrate formed with a deposition angle of 75° that shows the smallest signal intensity near 10 nm of film thickness in FIG. 10.

The aspect ratio of the plate-like metal fine structures (average length/average thickness) was calculated from the SEM image shown in FIG. 11, and the result showed that it was 2. This result shows that the aspect ratio of the plate-like metal fine structures (average length/average thickness) is preferably greater than or equal to two, as described above. The average length and the average thickness described above are, more specifically, calculated in the following manner. That is, extracting plate-like metal fine structure portions (portions indicated by dotted lines) in the SEM image of the cross-section view shown on the lower side of FIG. 6 by image processing, then elliptically approximating the extracted plate-like metal fine structure portions, and calculating an average of long axes of all ellipses appearing in the SEM image to calculate the average length, while calculating an average of short axes of all ellipses to calculate the average thickness.

The aspect ratio increases with an increase in the deposited film thickness, but if the size is excessively increased, plate-like metal fine structures contact each other and the sensitivity is reduced. Measurement of resistance of an optical field enhancement substrate with a deposited film thickness of 60 nm or more showed that the resistance value was less than or equal to 50Ω, being conductive, and it is considered that the sensitivity is reduced due to mutual contact of plate-like metal fine structures. Therefore, the deposited film thickness is preferably less than 60 nm, as described above.

What is claimed is:

1. An optical field enhancement device in which localized plasmon is induced on a surface through illumination of excitation light and intensity of signal light emitted, by the illumination, from a sample placed on the surface is enhanced, the device comprising:
   sharp-edged fine uneven structures disposed at random on a substrate; and
   metal flakes formed on tip portions of the sharp-edged fine uneven structures;
   the sharp-edged fine uneven structure being a structure in which the cross sectional area of a plane parallel to the substrate surface decreases as the distance from the substrate surface increases.

2. The optical field enhancement device of claim 1, wherein the metal flakes have a ratio of average length to average thickness greater than or equal to two.

3. The optical field enhancement device of claim 1, wherein the sharp-edged fine uneven structures are formed of a hydrate of a metal.

4. The optical field enhancement device of claim 3, wherein the metal is aluminum or titanium.

5. The optical field enhancement device of claim 1, wherein the sharp-edged fine uneven structures are formed of a hydrate of a metal oxide.

6. The optical field enhancement device of claim 5, wherein the metal oxide is an aluminum oxide, a titanium oxide, or a magnesium oxide.

7. The optical field enhancement device of claim 1, wherein the metal flakes are formed of gold, silver, copper, platinum, or aluminum.

8. The optical field enhancement device of claim 1, wherein a metal film formed of chromium, titanium, nickel, iron, silver, aluminum, germanium, or a metal suboxide is provided between the sharp-edged fine uneven structures and the metal flakes.

9. A manufacturing method of an optical field enhancement device in which localized plasmon is induced on a surface through illumination of excitation light and intensity of signal light emitted, by the illumination, from a sample placed on the surface is enhanced, the method comprising the steps of:

forming sharp-edged fine uneven structures disposed at random on a substrate; and forming metal flakes on tip portions of the sharp-edged fine uneven structures by depositing a metal from an oblique direction with respect to a direction perpendicular to a plane of the substrate on which the sharp-edged fine uneven structures are formed;

the sharp-edged fine uneven structure being a structure in which the cross sectional area of a plane parallel to the substrate surface decreases as the distance from the substrate increases.

10. The manufacturing method of an optical field enhancement device of claim 9, wherein the metal is deposited from a direction tilted greater than or equal to 65° with respect to the direction perpendicular to the plane of the substrate.

11. The manufacturing method of an optical field enhancement device of claim 9, wherein the metal is deposited with a deposited film thickness of 10 nm to less than 60 nm.

12. The manufacturing method of an optical field enhancement device of claim 9, wherein, before depositing the metal, chromium, titanium, nickel, iron, silver, aluminum, germanium, or a metal suboxide is deposited on the sharp-edged fine uneven structures.

\* \* \* \* \*